US005698986A

United States Patent [19]

Mays et al.

[11] Patent Number: 5,698,986
[45] Date of Patent: Dec. 16, 1997

[54] CIGARETTE DENSITY MONITOR

[75] Inventors: David L. Mays, Woodstock, Ga.; Ira B. Goldberg, Thousand Oaks, Calif.

[73] Assignee: Allen-Bradley Company, Inc., Milwaukee, Wis.

[21] Appl. No.: 600,076

[22] Filed: Feb. 12, 1996

[51] Int. Cl.$^6$ .......................... G01N 22/00; G01N 27/00; H01P 7/10; H03H 9/00
[52] U.S. Cl. ........................ 324/636; 324/642; 330/56; 333/227
[58] Field of Search ...................... 324/633, 636, 324/637, 642; 330/56; 333/219, 219.1, 227

[56] References Cited

U.S. PATENT DOCUMENTS

| | | | |
|---|---|---|---|
| 3,757,204 | 9/1973 | Hyde | 333/227 X |
| 3,783,373 | 1/1974 | Jawor | 324/639 |
| 4,350,883 | 9/1982 | Lagarde | 324/633 X |
| 4,700,145 | 10/1987 | Yelland et al. | 330/56 |
| 4,942,363 | 7/1990 | Lowitz | 324/631 |
| 5,027,090 | 6/1991 | Gueble et al. | 333/219.1 |
| 5,194,815 | 3/1993 | Maeno | 324/636 |

*Primary Examiner*—Glenn W. Brown
*Attorney, Agent, or Firm*—Tom Streeter; John M. Miller; John J. Horn

[57] ABSTRACT

A cylindrical microwave cavity 12 has a pinched center 28, 30. Two apertures 28, 30, one in the center of each face of the cylinder 10, provide access for a gas/powder mixture 124 having a dielectric coefficient depending on its density or some other measurement of interest. The faces 20, 22 of the cylinder 10 are much farther apart at the unpinched periphery, which comprises most of the volume of the cavity. The wider spacing allows an antenna 34 to be placed in the cavity 12, and provides a high Q-factor to maximize the sensitivity of the cavity 12. At the same time, certain resonance modes are greatly affected by a change in the dielectric coefficient of the gas/powder mixture 124 in the pinched portion 28, 30. The density of the powder or any other convenient variable may thus be servoed to any desired value. The powder 124 may be blown through the cavity 10, encased in tube 120 affixed to the cavity 12. Alternatively, the tube 104 may be formed around the powder 98, and the tube and powder passed through the cavity 12 together. This latter alternative is especially practical in the manufacture of tobacco cigarettes.

33 Claims, 5 Drawing Sheets

CIGARETTE DENSITY MONITOR

BACKGROUND OF THE INVENTION

The present invention relates to measuring the dielectric coefficient of a substance, and thereby measuring its density or other characteristic of interest, by measuring how the substance affects the resonance frequency of a microwave cavity. It has particular relation to measuring the dielectric coefficient of gas borne particles, since the low dielectric coefficient of most gasses requires the use of very high frequency radiation, which is expensive to produce. It has most particular relation to the manufacture of cigarettes, with the gas borne particles being air borne grains of tobacco.

The resonance frequency (or frequencies) of a microwave cavity depends on the size of the cavity and on the dielectric coefficient of the substance contained in the cavity. If the substance is a gas borne (generally air borne) powder or mass of particles, the resonance frequency will be different from the resonance frequency determined when only the gas is present. This will in turn indicate the density of the powder (air/powder ratio), or the relative proportions of two powders if a mixture is introduced into the cavity, or any of a number of other desired measurements.

The theory of calculating the resonance frequency is well developed, but often the quickest and most accurate way is simple experimentation. Several such experimental ways are available. First, one may sweep a variety of frequencies across the cavity bandwidth and determine the actual resonance frequency. Second, one may use an automatic frequency control (AFC) circuit to lock the cavity on resonance as the resonance frequency changes. Finally, and preferably for the cigarette density monitor application described herein, one may inject the resonance frequency for a cavity which contains only the carrier gas. Since this is not the resonance frequency of the gas/powder mixture, the cavity will not resonate as strongly. The diminution in resonance can be calibrated against known samples, and this calibration is then used to determine the measurement of interest of an unknown sample.

The resonance frequency is determined primarily by the dielectric coefficient of the carrying gas. Gasses generally have a lower dielectric constant than liquids or solids. The worker is therefore forced to use higher frequency radiation or larger cavities. The costs of producing radiation generally increases as the frequency increases. If the gas borne powder fills a large cavity, an indication is given only of the average dielectric constant of the similarly large quantity of powder. If the powder is confined only to a small portion of the cavity, then the sensitivity of the measurement suffers greatly.

SUMMARY OF THE INVENTION

The present invention overcomes this problem by using a cylindrical cavity with a pinched center. A circular cavity is preferred, but the cavity may be elliptical, rectangular, or any other desired shape. Two apertures, one in the center of each face of the cylinder, provide access for the gas/powder mixture. The faces are much farther apart at the unpinched periphery, which comprises most of the volume of the cavity.

The wider spacing somewhat reduces the operating frequency, and therefore allows less expensive radiation to be used. More importantly, it allows an antenna to be placed in the cavity, which introduces more radiation into the cavity for a given power of radiation source. Further, the larger volume in the outer regions provides a higher Q-factor. High Q-factors provide a greater electric field strength throughout the entire cavity. Pinching the center further increases the electric field in the pinched region. Certain resonance modes will therefore show great sensitivity to a change in the dielectric coefficient in the pinched portion. This sensitivity is not despite, but because, the volume of the gas/powder mixture is so small. These modes are easily determined by sweeping a desired frequency range twice, once when the pinched portion is empty (gas only), and a second time when it is full (powder only). The frequency showing the greatest amplitude difference between the full and empty conditions is the center of the preferred resonance band. The preferred operating frequency lies on the most linear portion of one of the shoulders of this band, as describe in more detail below.

Measurement is the broadest use of the present invention, but control—especially packaging control—is the most valuable use. The flow rate of the powder, the gas/powder ratio, or any other convenient variable may readily be servoed to any desired value. The powder may be blown through the cavity, encased in tube affixed to the cavity. Alternatively, the tube may be formed around the powder, and the tube and powder passed through the cavity together.

This latter alternative is especially practical in the manufacture of tobacco cigarettes. Modern cigarette manufacturing machines produce a continuous paper and tobacco rod, which is cut into individual cigarettes by downstream apparatus. The density of the tobacco in the rod must be continuously measured, with the measurements servoed back to the manufacturing machine.

The present state of the art places a radioactive source next to the emerging rod, and measures how much of the nuclear radiation makes it through the rod. The typical cigarette consumer prefers to avoid nuclear radiation. No such distaste attaches, however, to the microwaves which cook his food and operate his cellular telephone.

DETAILED DESCRIPTION OF THE DRAWINGS

Figure 1:
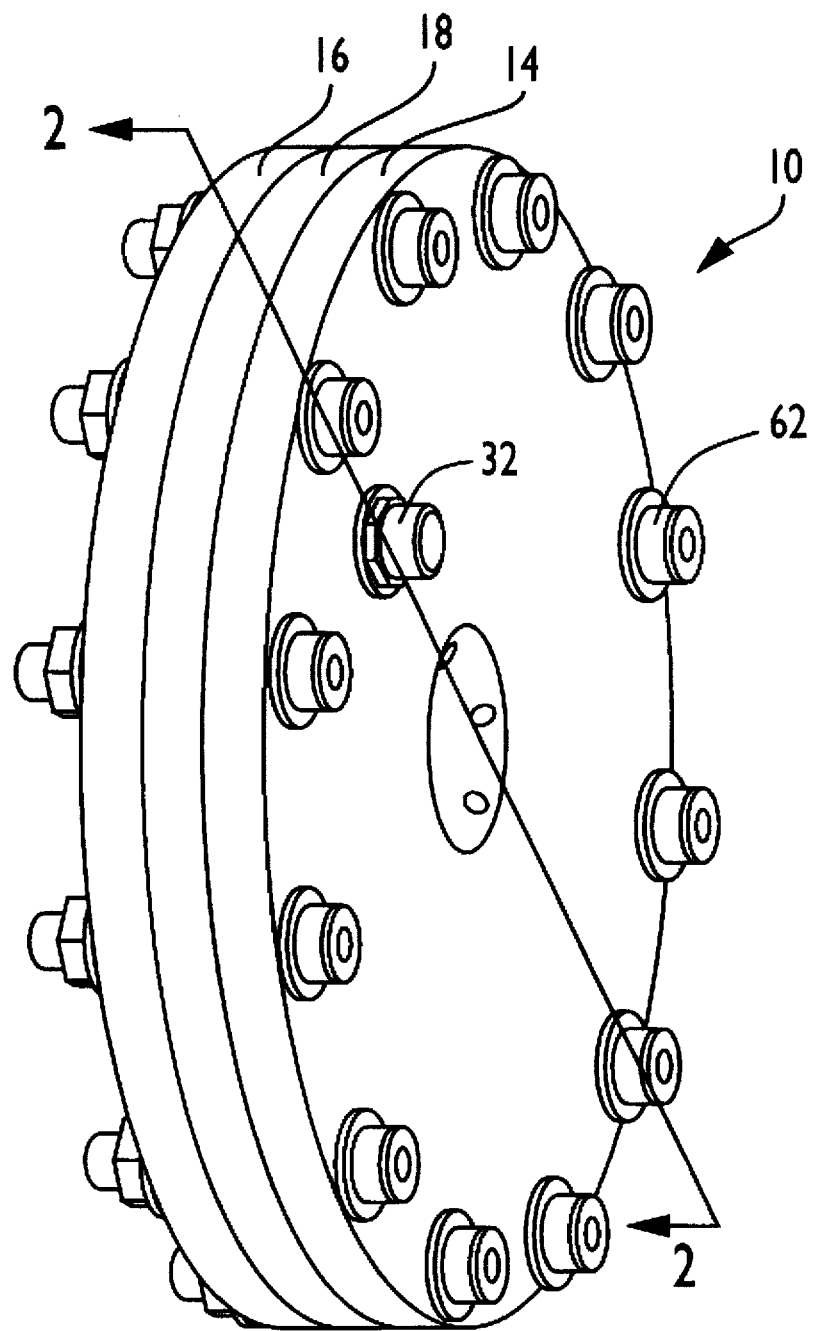
FIG. 1 is a perspective view of the cavity used in the present invention.
Figure 2:
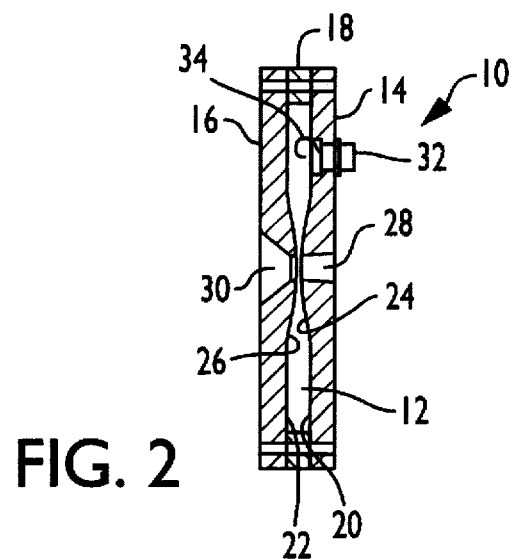
FIG. 2 is a cross section of the cavity of FIG. 1, taken along lines 2—2.

In FIGS. 1 and 2, an essentially cylindrical container 10 surrounding a resonant cavity 12 is formed from a first side plate (first member) 14, a second side plate (second member) 16, and a body (third member) 18. The cylinder is preferably circular, but the cylinder may be elliptical, rectangular, or any other desired shape. The first and second members 14, 16 each define a conductive annular surface 20, 22, a conductive frusto-conical surface 24, 16, and a central first aperture 18 or second aperture 30. The cone of the conductive frusto-conical surface 24, 26 is also preferably circular, but also may be elliptical, rectangular, or any other desired shape.

The first member 14 also includes a third aperture 32, which allows microwaves to be injected into, or reflected out of, the cavity 12. The third apertue 32 includes an antenna 34, or other suitable coupling or impedance matching device. The antenna 34 may be a loop, as shown. If desired, if may instead be a probe, namely, a metal rod from the center conductor of a coaxial cable attached to the first member 14 at the third aperture 32. It may even be the open end of a waveguide. In this last embodiment, the conductive annular surfaces 20, 22 are not separated to accommodate the antenna 34, but only to provide the many other advantages described above. If desired, the third aperture 32 may be included in the second member 16 or third member 18 rather than in the first member 14.

Figure 3:
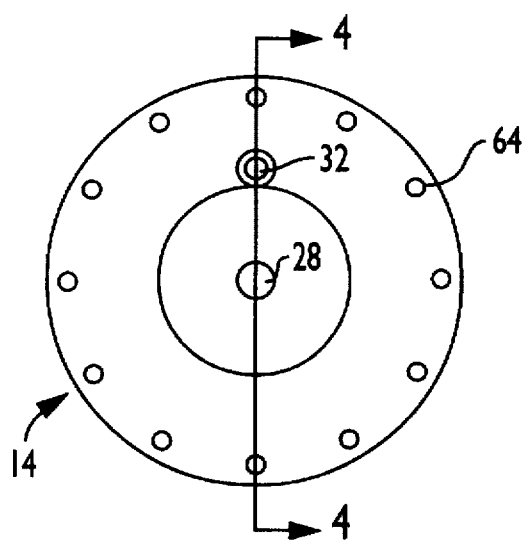
FIG. 3 is a plan view of the cavity side plate which supports the connector to the microwave source.
Figure 4:
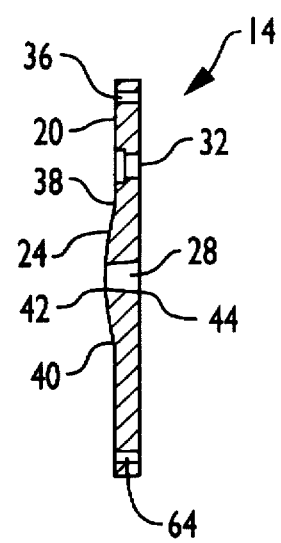
FIG. 4 is a cross section of the side plate of FIG. 3, taken along lines 4—4.

FIGS. 3 and 4 show the first member 14 in greater detail. The annular surface 20 has an outer edge 36 and an inner edge 38. The frusto-conical surface 24 has an outer edge 40 and an inner edge 42. The outer edge 40 of the frusto-conical surface 38 is conductively attached to the inner edge 24 of the annular surface 20. The inner edge 42 of the frusto-conical surface 38 forms the inner edge of the first aperture 28. The outer edge 44 of the first aperture 28 lies on the exterior edge of the first member 14.

Figure 5:
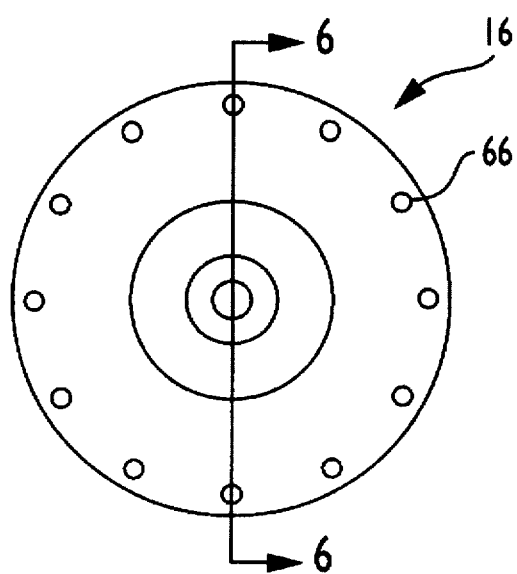
FIG. 5 is a plan view of the cavity side plate which provides an entrance to the gas/powder mixture.
Figure 6:
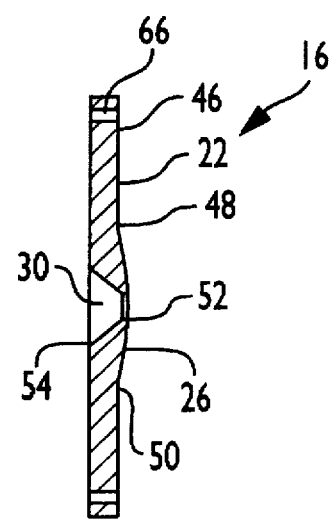
FIG. 6 is a cross section of the side plate of FIG. 5, taken along lines 6—6.

FIGS. 5 and 6 show the second member 16 in greater detail. The annular surface 22 has an outer edge 46 and an inner edge 48. The frusto-conical surface 26 has an outer edge 50 and an inner edge 52. The outer edge 50 of the frusto-conical surface 26 is conductively attached to the inner edge 48 of the annular surface 22. The inner edge 52 of the frusto-conical surface 26 forms the inner edge of the second apertue 30. The outer edge 54 of the second aperture 30 lies on the exterior edge of the second member 16.

Figure 7:
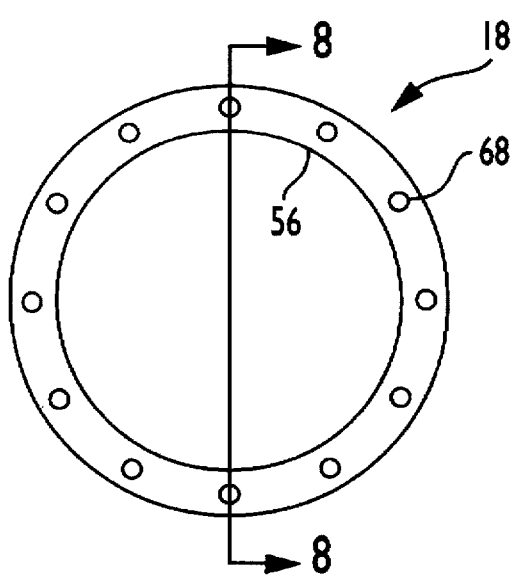
FIG. 7 is a plan view of the body which separates the two side plates.
Figure 8:
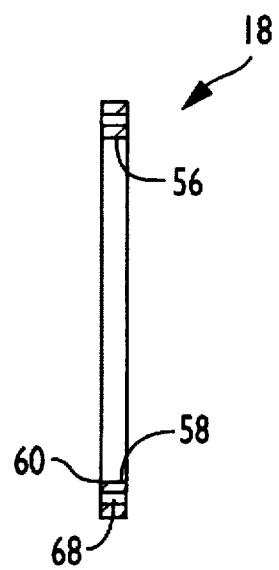
FIG. 8 is a cross section of the body of FIG. 7, taken along lines 8—8.

FIGS. 7 and 8 show the third member 18 in greater detail. It is a cylindrical body with an inner surface 56. The inner surface 56 has a first edge 58 conductively attached to the exterior edge 36 of the first annular surface 20, and has a second edge 60 conductively attached to the exterior edge 46 of the second annular surface 22. This attachment is conveniently provided by bolts 62 going through bolt holes 64, 66, and 68 of first, second, and third members 14, 16, and 18, respectively.

Figure 9:
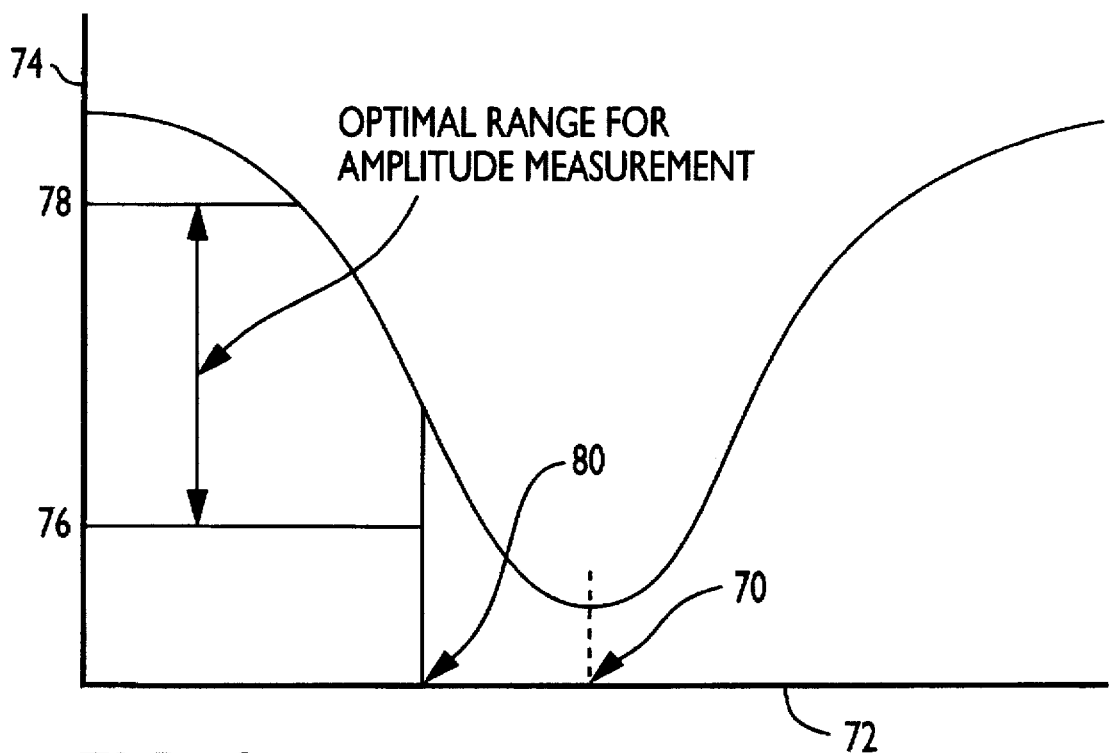
FIG. 9 is a graph of frequency vs. reflected power at and near a resonance frequency of the empty cavity.

FIG. 9 is a graph of frequency vs. reflected power at and near a resonance frequency of the empty cavity 12. At the empty cavity resonance frequency 70, almost all of the power of the incoming signal is consumed in the resonance, and little is reflected back out of the cavity 12. As the actual frequency 72 deviates from the empty cavity resonance frequency 70, the reflected power 74 gets larger and larger. Between ten percent reflected power 76, and fifty percent reflected power 78, the reflected power 74 is almost linear with respect to the frequency 72. Any convenient operating frequency 80 may be selected in this band. Variations in the amount or density of powder cause variations in the resonance frequency, and therefore cause variations in the amount of reflected power 74, just as though the operating frequency 80 had changed instead.

It is generally best to experimentally calibrate the amount or density of the powder directly with amount of reflected power 74, rather than attempting to calculate a calibration based on a phantom shift in the empty cavity resonance frequency 70 or in the operating frequency 80. The foregoing linearizing method of selecting the operating frequency 80 is used only because it produces an experimental calibration of powder density vs. reflected power which is also approximately linear.

Figure 10:
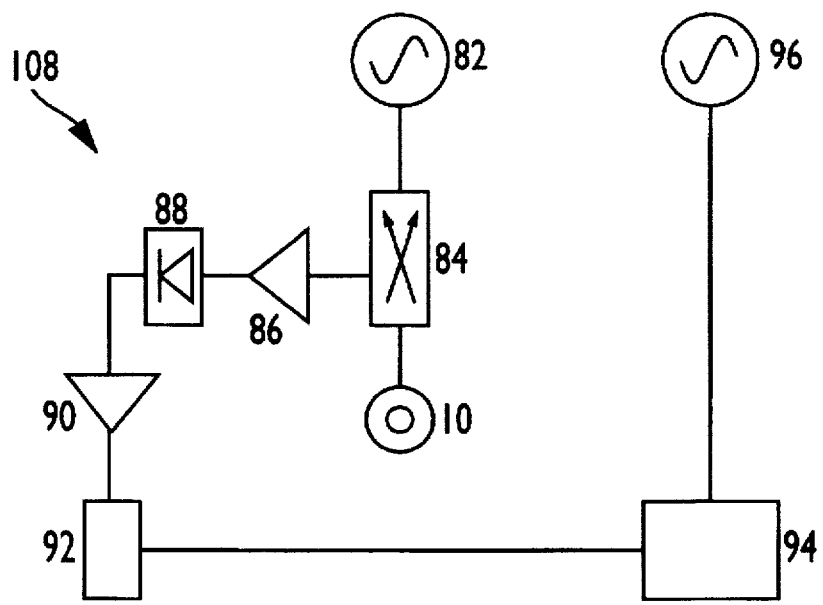
FIG. 10 is a schematic drawing of the entire sensor, including both the cavity and the electronics associated with it.

FIG. 10 is a schematic drawing of the entire sensor, including both the cavity and the electronics associated with it. A radiation source 82 source injects radiation into a coupler 84, which passes it on to the sensor 10. Radio frequency (RF) or microwave (MW) is preferred, but any suitable frequency may be used. The portion of the radiation reflected from the sensor 10 is passed by the coupler 84 to a first (generally RF or MW) amplifier 86. The amplified signal is converted to dc-voltage by a detector 88, and the converted signal is amplified by a second amplifier 90. The output of the second amplifier 90 is digitized by an analog-to-digital converter (ADC) 92, and the digitized signal is passed to a microprocessor 94.

A shaft encoder 96 also passes a signal to the microprocessor 94. The shaft encoder 96 is so called because the typical cigarette manufacturing machine includes a shaft whose position indicates the stage of processing of the cigarette under consideration. A typical shaft may have one full revolution for every four cigarettes. The density of the tobacco typically needs to be measured in thirty-two different locations. The shaft encoder therefore indicates, one hundred and twenty-eight times per revolution, that a location of interest is present within the sensor. The microprocessor 94 notes this fact (extracting this fact from a larger volume of data produced by the shaft encoder 96 if necessary), and strobes the ADC 92 to digitize the signal at that moment. If the production rate of cigarettes can be increased, the sampling frequency should be similarly increased.

A digitized signal may be produced at more frequent intervals, without strobing. However, the use of shorter intervals may require a more complex and expensive ADC 92. It is ultimately a design issue as to whether a low frequency ADC 92 should be strobed at the moments of interest or whether the output of a high frequency ADC 92 should be examined at the moments of interest. "Strobe the ADC" therefore includes "examine the output of the ADC" as used in the present application.

Figure 11:
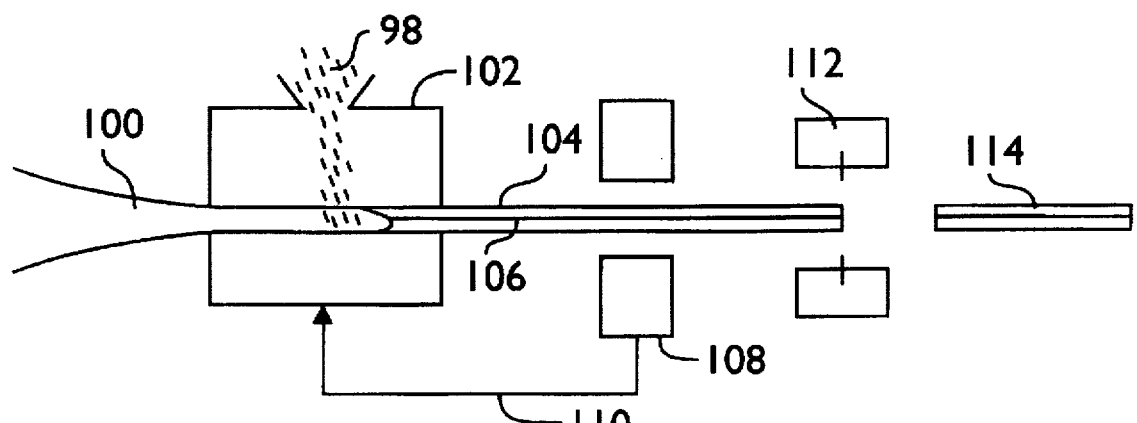
FIG. 11 is a schematic drawing of a complete cigarette manufacturing apparatus, including both the sensor of FIG. 10 and the machinery associated with it.

In FIG. 11, air borne grains of tobacco 98 and a sheet of cigarette paper 100 are applied to a cigarette manufacturing machine 102. The machine 102 seals the grains 98 into a continuous rod 104, formed by sealing the edges of the paper 100 into a seal 106. The rod 104 passes through the sensor 10 (including its associated electronics 108). A control signal from the microprocessor 94 is fed back in a feed back loop 110 to the machine 102 whenever the reflected power 74 goes above an upper control limit or below a lower control limit. When the rod 104 emerges from the sensor 10, a cutter 112 cuts it into individual cigarettes 114.

If desired, the reflected power 74 may first be converted by the microprocessor 94 into the density of the tobacco 98 in the rod 104, or into any other measurement of interest. As before, a direct experimental calibration using known samples, with known measurements of interest, is preferred.

Powders or particles other than tobacco grains 98 may be used in other applications, and the sheet may be other than cigarette paper 100 in those applications. Likewise, the feed back loop 110 may be omitted if only measurement, and not control, is desired.

Figure 12:
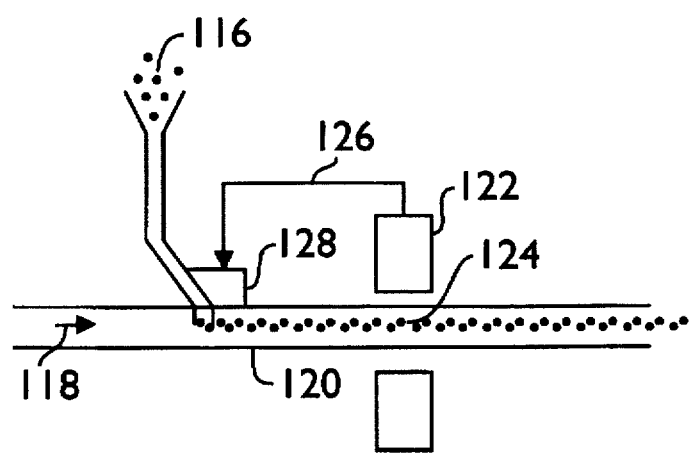
FIG. 12 is a variation on FIG. 11.

FIG. 12 is a variation on FIG. 11. Particles 116 are fed into a gas stream 118, the gas stream 118 being contained in a tube 120. The sensor and associated electronics 122 measures the resulting gas borne particles 124 and sends a signal via feed back loop 126 to a valve or similar regulator 128, which determines how fast the particles 116 shall be added to the gas stream 118. The result is a controlled flow of gas borne particles 124.

As before, the feedback loop 126 may be omitted if only measurement, and not control, is desired.

SCOPE OF THE INVENTION

While several embodiments have been described in some detail, the true scope and spirit of the present invention is not limited thereto, but is limited only by the appended claims and their equivalents.

What is claimed is:

1. Means defining a resonant cavity, the means comprising:

(a) a first member comprising:

(1) means defining a conductive first annular surface, the conductive first annular surface having an interior edge and an exterior edge;

(2) means defining a conductive first frusto-conical surface, the conductive first frusto-conical surface having an interior edge and an exterior edge, the exterior edge of the conductive first frusto-conical surface being conductively attached to the interior edge of the conductive first annular surface; and (3) means defining a first apertue, the first apertue having an interior edge and an exterior edge, the interior edge of the first aperture being conductively attached to the interior edge of the conductive first frusto-conical surface, and the exterior edge of the first apertue being conductively attached to an exterior surface of the means defining a conductive first annular surface;

(b) a second member comprising:

(1) means defining a conductive second annular surface, the conductive second annular surface having an interior edge and an exterior edge;

(2) means defining a conductive second frusto-conical surface, the conductive second frusto-conical surface having an interior edge and an exterior edge, the exterior edge of the conductive second frusto-conical surface being conductively attached to the interior edge of the conductive second annular surface; and (3) means defining a second apertue, the second apertue having an interior edge and an exterior edge, the interior edge of the second apertue being conductively attached to the interior edge of/he conductive second frusto-conical surface, and the exterior edge of the second apertue being conductively attached to an exterior surface of the means defining a conductive second annular surface;

wherein:

(4) the conductive first annular surface is disposed coaxially with, and parallel to, the conductive second annular surface, at a surface separation distance; and (5) the interior edge of the conductive second frusto-conical surface and the interior edge of the conductive second frusto-conical surface are disposed opposite each other, and have a separation from each other which is less than the surface separation distance;

(c) a third member comprising means defining a conductive cylindrical side wall surface, wherein:

(1) the conductive cylindrical side wall surface has a first edge conductively attached to the exterior edge of the conductive first annular surface; and (2) the conductive cylindrical side wall surface has a second edge conductively attached to the exterior edge of the conductive second annular surface; and (d) means defining a third aperture into and out of the resonant cavity, the third aperture being configured to transmit radiation having a frequency near a resonance frequency of the resonant cavity.

2. The means of claim 1, wherein the means defining the third aperture into and out of the resonant cavity are included within the means defining the conductive first annular surface.

3. The means of claim 1, wherein the means defining the third aperture into and out of the resonant cavity are included within the means defining the conductive cylindrical side wall surface.

4. Apparatus for packaging gas borne particles, the apparatus comprising the apparatus of claim 1, and further comprising:

(a) means for forming a rod by forming a sheet into a robe and inserting gas borne particles into the robe as it is formed, the forming means being situated to insert the rod formed by it into the first and second apertures of the resonant cavity;

(b) a coupler, connected to transmit radiation into and out of the third aperture of the resonant cavity, the radiation having a frequency near a resonance frequency of the resonant cavity;

(c) a radiation source, the radiation having the frequency near the resonance frequency of the resonant cavity, and the radiation source being connected to inject radiation into the coupler;

(d) a radiation amplifier, connected to the coupler and constructed:

(1) to amplify; and (2) to convert to a voltage signal;

radiation reflected from the resonant cavity into the coupler;

(e) a detector:

(1) connected to the radiation amplifier; and (2) constructed to convert the voltage signal from the radiation amplifier to dc-voltage;

(f) a voltage amplifier connected to an output of the detector;

(g) an analog-to-digital converter (ADC) connected to digitized an output of the voltage amplifier;

(h) a microprocessor connected to convert an output of the ADC to a desired measurement of the rod inserted through the first and second apertures of the resonant cavity;

(i) a shaft encoder constructed to encode a position of a shaft which rotates through a known angle for each package to be produced from the rod, wherein:

(1) an output of the shaft encoder drives the microprocessor;

(2) the microprocessor, in response to the output from the shaft encoder, strobes the ADC to give an output whenever a portion of interest of the rod lies between the first and second apertures of the resonant cavity; and (3) the forming means is connected to respond to a control signal from the microprocessor, adding more particles to the rod when the control signal indicates that the desired measurement of a comparable portion of a previous package is below a lower control limit, and adding fewer particles to the rod when the control signal indicates that the desired measurement of a comparable portion of a previous package is above an upper control limit; and (j) means for cutting an individual package from the rod.

5. The apparatus of claim 4, wherein the means defining the third aperture into and out of the resonant cavity are included within the means defining the conductive first annular surface.

6. The apparatus of claim 5, wherein:

(a) the package comprises a cigarette;

(b) the particles comprise grains of tobacco; and (c) the sheet comprises cigarette paper.

7. The apparatus of claim 4, wherein the means defining the third aperture into and out of the resonant cavity are included within the means defining the conductive cylindrical side wall surface.

8. The apparatus of claim 7, wherein:

(a) the package comprises a cigarette;

(b) the particles comprise grains of tobacco; and (c) the sheet comprises cigarette paper.

9. The apparatus of claim 4, wherein:

(a) the package comprises a cigarette;

(b) the particles comprise grains of tobacco; and (c) the sheet comprises cigarette paper.

10. Apparatus for measuring gas borne particles, the apparatus comprising:

(a) means defining a resonant cavity, the means comprising:

(1) a first member comprising:

(A) means defining a conductive first annular surface, the conductive first annular surface having an interior edge and an exterior edge;

(B) means defining a conductive first frusto-conical surface, the conductive first frusto-conical surface having an interior edge and an exterior edge, the exterior edge of the conductive first frusto-conical surface being conductively attached to the interior edge of the conductive first annular surface; and (C) means defining a first aperture, the first apertue having an interior edge and an exterior edge, the interior edge of the first apertue being conductively attached to the interior edge of the conductive first frusto-conical surface, and the exterior edge of the first aperture being conductively attached to an exterior surface of the means defining a conductive first annular surface;

(2) a second member comprising:

(A) means defining a conductive second annular surface, the conductive second annular surface having an interior edge and an exterior edge;

(B) means defining a conductive second frusto-conical surface, the conductive second frusto-conical surface having an interior edge and an exterior edge, the exterior edge of the conductive second frusto-conical surface being conductively attached to the interior edge of the conductive second annular surface; and (C) means defining a second apertue, the second aperture having an interior edge and an exterior edge, the interior edge of the second aperture being conductively attached to the interior edge of the conductive second frusto-conical surface, and the exterior edge of the second aperture being conductively attached to an exterior surface of the means defining a conductive second annular surface;

wherein:

(D) the conductive first annular surface is disposed coaxially with, and parallel to, the conductive second annular surface, at a surface separation distance; and (E) the interior edge of the conductive second frusto-conical surface and the interior edge of the conductive second frusto-conical surface are disposed opposite each other, and have a separation from each other which is less than the surface separation distance;

(3) a third member comprising means defining a conductive cylindrical side wall surface, wherein:

(A) the conductive cylindrical side wall surface has a first edge conductively attached to the exterior edge of the conductive first annular surface; and (B) the conductive cylindrical side wall surface has a second edge conductively attached to the exterior edge of the conductive second annular surface; and (4) means defining a third aperture into and out of the resonant cavity, the third aperture being configured to transmit radiation having a frequency near a resonance frequency of the resonant cavity;

(b) a tube, adapted to contain gas borne particles, passing through the first and second apertures of the resonant cavity;

(c) a coupler, connected to transmit radiation having the frequency near the resonance frequency of the resonant cavity into and out of the third aperture of the resonant cavity;

(d) a radiation source:

(1) constructed to produce radiation having the frequency near the resonance frequency of the resonant cavity; and (2) connected to inject the radiation into the coupler;

(e) a radiation amplifier, connected to the coupler and constructed to:

(1) amplify; and (2) convert to a voltage signal;

radiation reflected from the resonant cavity into the coupler;

(f) a detector:

(1) connected to the radiation amplifier; and (2) constructed to convert the voltage signal from the amplifier to dc-voltage;

(g) a voltage amplifier connected to an output of the detector;

(h) an analog-to-digital converter (ADC) connected to digitized an output of the voltage amplifier; and (i) a microprocessor connected to convert an output of the ADC to a desired measurement of gas borne particles in the tube.

11. The apparatus of claim 10, wherein the means defining the third aperture into and out of the resonant cavity are included within the means defining the conductive first annular surface.

12. The apparatus of claim 10, wherein the means defining the third aperture into and out of the resonant cavity are included within the means defining the conductive cylindrical side wall surface.

13. Apparatus for controlling gas borne particles, the apparatus comprising the apparatus of claim 10, and further comprising:

(a) means for inserting gas into the tube; and
(b) means, responsive to a control signal from the microprocessor, for adding more particles to the tube when the control signal indicates that the desired measurement is below a lower control limit, and for adding fewer particles to the tube when the control signal indicates that the desired measurement is above an upper control limit.

14. The apparatus of claim 13, wherein the means defining the third aperture into and out of the resonant cavity are included within the means defining the conductive first annular surface.

15. The apparatus of claim 13, wherein the means defining the third aperture into and out of the resonant cavity are included within the means defining the conductive cylindrical side wall surface.

16. A method for measuring gas borne particles, the method comprising the steps of:
(a) defining a resonant cavity from means comprising:
 (1) a first member comprising:
  (A) means defining a conductive first annular surface, the conductive first annular surface having an interior edge and an exterior edge;
  (B) means defining a conductive first frusto-conical surface, the conductive first frusto-conical surface having an interior edge and an exterior edge, the exterior edge of the conductive first frusto conical surface being conductively attached to the interior edge of the conductive first annular surface; and
  (C) means defining a first aperture, the first aperture having an interior edge and an exterior edge, the interior edge of the first aperture being conductively attached to the interior edge of the conductive first frusto-conical surface, and the exterior edge of the first aperture being conductively attached to an exterior surface of the means defining a conductive first annular surface;
 (2) a second member comprising:
  (A) means defining a conductive second annular surface, the conductive second annular surface having an interior edge and an exterior edge;
  (B) means defining a conductive second frusto-conical surface, the conductive second frusto-conical surface having an interior edge and an exterior edge, the exterior edge of the conductive second frusto-conical surface being conductively attached to the interior edge of the conductive second annular surface; and
  (C) means defining a second apertue, the second aperture having an interior edge and an exterior edge, the interior edge of the second aperture being conductively attached to the interior edge of the conductive second frusto-conical surface, and the exterior edge of the second aperture being conductively attached to an exterior surface of the means defining a conductive second annular surface;
  wherein:
  (D) the conductive first annular surface is disposed co axially with, and parallel to, the conductive second annular surface, at a surface separation distance; and
  (E) the interior edge of the conductive second frusto-conical surface and the interior edge of the conductive second frusto-conical surface are disposed opposite each other, and have a separation from each other which is less than the surface separation distance;
 (3) a third member comprising means defining a conductive cylindrical side wall surface, wherein:
  (A) the conductive cylindrical side wall surface has a first edge conductively attached to the exterior edge of the conductive first annular surface; and
  (B) the conductive cylindrical side wall surface has a second edge conductively attached to the exterior edge of the conductive second annular surface; and
 (4) means defining a third aperture into and out of the resonant cavity, the third aperture being configured to transmit radiation having a frequency near a resonance frequency of the resonant cavity;
(b) bearing the particles on a gas through a robe through the first and second apertures of the resonant cavity;
(c) creating radiation in a radiation source, the radiation having a frequency near a resonance frequency of the resonant cavity;
(d) injecting the radiation through a coupler and into and out of the third aperture of the resonant cavity;
(e) amplifying radiation reflected from the resonant cavity into the coupler;
(f) converting the amplified radiation to a voltage signal;
(g) converting the voltage signal to a dc-voltage;
(h) amplifying the dc-voltage;
(i) digitizing the amplified dc-voltage with an analog-to-digital converter (ADC); and
(j) converting, in a microprocessor, the digitized dc-voltage to a desired measurement of the gas borne particles in the robe.

17. The method of claim 16, wherein the means defining the third aperture into and out of the resonant cavity are included within the means defining the conductive first annular surface.

18. The method of claim 16, wherein the means defining the third aperture into and out of the resonant cavity are included within the means defining the conductive cylindrical side wall surface.

19. A method for controlling gas borne particles, the method comprising the method of claim 16, and further comprising the steps of:
(a) inserting gas into the tube; and
(b) in response to a control signal from the microprocessor:
 (1) adding more particles to the tube when the control signal indicates that the desired measurement is below a lower control limit, and
 (2) adding fewer particles to the tube when the control signal indicates that the desired measurement is above an upper control limit.

20. The method of claim 19, wherein the means defining the third apertue into and out of the resonant cavity are included within the means defining the conductive first annular surface.

21. The method of claim 19, wherein the means defining the third aperture into and out of the resonant cavity are included within the means defining the conductive cylindrical side wall surface.

22. A method for packaging gas borne particles, the method comprising the steps of:

(a) defining a resonant cavity from means comprising:

(1) a first member comprising:

(A) means defining a conductive first annular surface, the conductive first annular surface having an interior edge and an exterior edge;

(B) means defining a conductive first frusto-conical surface, the conductive first frusto-conical surface having an interior edge and an exterior edge, the exterior edge of the conductive first frusto-conical surface being conductively attached to the interior edge of the conductive first annular surface; and (C) means defining a first aperture, the first aperture having an interior edge and an exterior edge, the interior edge of the first aperture being conductively attached to the interior edge of the conductive first frusto-conical surface, and the exterior edge of the first aperture being conductively attached to an exterior surface of the means defining a conductive first annular surface;

(2) a second member comprising:

(A) means defining a conductive second annular surface, the conductive second annular surface having an interior edge and an exterior edge;

(B) means defining a conductive second frusto-conical surface, the conductive second frusto-conical surface having an interior edge and an exterior edge, the exterior edge of the conductive second frusto-conical surface being conductively attached to the interior edge of the conductive second annular surface; and (C) means defining a second apertue, the second apertue having an interior edge and an exterior edge, the interior edge of the second aperture being conductively attached to the interior edge of the conductive second frusto-conical surface, and the exterior edge of the second aperture being conductively attached to an exterior surface of the means defining a conductive second annular surface;

wherein:

(D) the conductive first annular surface is disposed coaxially with, and parallel to, the conductive second annular surface, at a surface separation distance; and (E) the interior edge of the conductive second frusto-conical surface and the interior edge of the conductive second frusto-conical surface are disposed opposite each other, and have a separation from each other which is less than the surface separation distance;

(3) a third member comprising means defining a conductive cylindrical side wall surface, wherein:

(A) the conductive cylindrical side wall surface has a first edge conductively attached to the exterior edge of the conductive first annular surface; and (B) the conductive cylindrical side wall surface has a second edge conductively attached to the exterior edge of the conductive second annular surface; and (4) means defining a third apertue into and out of the resonant cavity, the third aperture being configured to transmit radiation having a frequency near a resonance frequency of the resonant cavity;

(b) forming a rod by forming a sheet into a robe and inserting gas borne particles into the tube as it is formed;

(c) inserting the rod through the first and second apertures of the resonant cavity;

(d) creating radiation in a radiation source, the radiation having a frequency near a resonance frequency of the resonant cavity;

(e) injecting the radiation through a coupler and into and out of the third aperture of the resonant cavity;

(f) amplifying radiation reflected from the resonant cavity into the coupler;

(g) converting the amplified radiation to a voltage signal;

(h) converting the voltage signal to a dc-voltage;

(i) amplifying the &-voltage;

(j) digitizing the amplified dc-voltage with an analog-to-digital converter (ADC);

(k) converting, in a microprocessor, the digitized tic-voltage to a desired measurement of the rod inserted through the first and second apertures of the resonant cavity;

(l) coding a position of a shaft which rotates through a known angle for each package to be produced from the rod;

(m) applying a shaft position code to the microprocessor;

(n) programming the microprocessor, in response to the output from the shaft encoder, to strobe the ADC to give an output whenever a portion of interest of the rod lies between the first and second apertures of the resonant cavity;

(o) controlling the forming of the rod, in response to a control signal from the microprocessor, by adding more particles to the rod when the control signal indicates that the desired measurement of a comparable portion of a previous package is below a lower control limit, and adding fewer particles to the rod when the control signal indicates that the desired measurement of a comparable portion of a previous package is above an upper control limit; and (p) cutting an individual package from the rod.

23. The method of claim 22, wherein the means defining the third aperture into and out of the resonant cavity are included within the means defining the conductive first annular surface.

24. The method of claim 23, wherein:

(a) the package comprises a cigarette;

(b) the particles comprise grains of tobacco; and (c) the sheet comprises cigarette paper.

25. The method of claim 22, wherein the means defining the third aperture into and out of the resonant cavity are included within the means defining the conductive cylindrical side wall surface.

26. The method of claim 25, wherein:

(a) the package comprises a cigarette;

(b) the particles comprise grains of tobacco; and (c) the sheet comprises cigarette paper.

27. The method of claim 22, wherein:

(a) the package comprises a cigarette;

(b) the particles comprise grains of tobacco; and (c) the sheet comprises cigarette paper.

28. A package of particles manufactured by a process comprising the steps of (a) defining a resonant cavity from means comprising:

(1) a first member comprising:

(A) means defining a conductive first annular surface, the conductive first annular surface having an interior edge and an exterior edge;

(B) means defining a conductive first frusto-conical surface, the conductive first frusto-conical surface having an interior edge and an exterior edge, the exterior edge of the conductive first frusto-conical surface being conductively attached to the interior edge of the conductive first annular surface; and (C) means defining a first aperture, the first apertue having an interior edge and an exterior edge, the interior edge of the first aperture being conductively attached to the interior edge of the conductive first frusto-conical surface, and the exterior edge of the first apertue being conductively attached to an exterior surface of the means defining a conductive first annular surface;

(2) a second member comprising:

(A) means defining a conductive second annular surface, the conductive second annular surface having an interior edge and an exterior edge;

(B) means defining a conductive second frusto-conical surface, the conductive second frusto-conical surface having an interior edge and an exterior edge, the exterior edge of the conductive second frusto-conical surface being conductively attached to the interior edge of the conductive second annular surface; and (C) means defining a second aperture, the second aperture having an interior edge and an exterior edge, the interior edge of the second aperture being conductively attached to the interior edge of the conductive second frusto-conical surface, and the exterior edge of the second apertue being conductively attached to an exterior surface of the means defining a conductive second annular surface;

wherein:

(D) the conductive first annular surface is disposed coaxially with, and parallel to, the conductive second annular surface, at a surface separation distance; and (E) the interior edge of the conductive second frusto-conical surface and the interior edge of the conductive second frusto-conical surface are disposed opposite each other, and have a separation from each other which is less than the surface separation distance;

(3) a third member comprising means defining a conductive cylindrical side wall surface, wherein:

(A) the conductive cylindrical side wall surface has a first edge conductively attached to the exterior edge of the conductive first annular surface; and (B) the conductive cylindrical side wall surface has a second edge conductively attached to the exterior edge of the conductive second annular surface; and (4) means defining a third aperture into and out of the resonant cavity, the third aperture being configured to transmit radiation having a frequency near a resonance frequency of the resonant cavity;

(b) forming a rod by forming a sheet into a tube and inserting gas borne particles into the tube as it is formed;

(c) inserting the rod through the first and second apertures of the resonant cavity;

(d) creating radiation in a radiation source, the radiation having a frequency near a resonance frequency of the resonant cavity;

(e) injecting the radiation through a coupler and into and out of the third aperture of the resonant cavity;

(f) amplifying radiation reflected from the resonant cavity into the coupler;

(g) converting the amplified radiation to a voltage signal;

(h) converting the voltage signal to a dc-voltage;

(i) amplifying the dc-voltage;

(j) digitizing the amplified dc-voltage with an analog-to-digital converter (ADC);

(k) converting, in a microprocessor, the digitized dc-voltage to a desired measurement of the rod inserted through the first and second apertures of the resonant cavity;

(l) coding a position of a shaft which rotates through a known angle for each package to be produced from the rod:

(n) applying a shaft position code to the microprocessor;

(o) programming the microprocessor, in response to the output from the shaft encoder, to strobe the ADC to give an output whenever a portion of interest of the rod lies between the first and second apertures of the resonant cavity;

(p) controlling the forming of the rod, in response to a control signal from the microprocessor, by adding more particles to the rod when the control signal indicates that the desired measurement of a comparable portion of a previous package is below a lower control limit, and adding fewer particles to the rod when the control signal indicates that the desired measurement of a comparable portion of a previous package is above an upper control limit; and (o) cutting an individual package from the rod.

29. The package of claim 28, wherein the means defining the third aperture into and out of the resonant cavity are included within the means defining the conductive first annular surface.

30. The package of claim 29, wherein:

(a) the package comprises a cigarette;

(b) the particles comprise grains of tobacco; and (c) the sheet comprises cigarette paper.

31. The package of claim 28, wherein the means defining the third aperture into and out of the resonant cavity are included within the means defining the conductive cylindrical side wall surface.

32. The package of claim 31, wherein:

(a) the package comprises a cigarette;

(b) the particles comprise grains of tobacco; and (c) the sheet comprises cigarette paper.

33. The package of claim 28, wherein:

(a) the package comprises a cigarette;

(b) the particles comprise grains of tobacco; and (c) the sheet comprises cigarette paper.

* * * * *